United States Patent
Wulf

(10) Patent No.: US 6,172,785 B1
(45) Date of Patent: Jan. 9, 2001

(54) LIGHT-SCANNING DEVICE

(75) Inventor: Jürgen Wulf, Ueberlingen (DE)

(73) Assignee: Bodenseewerk Perkin-Elmer GmbH, Ueberlingen (DE)

(*) Notice: Under 35 U.S.C. 154(b), the term of this patent shall be extended for 0 days.

(21) Appl. No.: 09/380,011

(22) PCT Filed: Dec. 4, 1997

(86) PCT No.: PCT/EP97/06792

§ 371 Date: Nov. 19, 1999

§ 102(e) Date: Nov. 19, 1999

(87) PCT Pub. No.: WO98/38497

PCT Pub. Date: Sep. 3, 1998

(30) Foreign Application Priority Data

Feb. 24, 1997 (DE) .............................................. 197 07 225

(51) Int. Cl.[7] .................................................. G02B 26/08
(52) U.S. Cl. .......................... 359/196; 359/201; 359/202; 359/206; 359/393; 356/317
(58) Field of Search .................................... 359/201, 202, 359/204–206, 368, 380, 391, 393; 250/201.2–201.4; 356/311, 317, 318

Primary Examiner—James Phan

(74) Attorney, Agent, or Firm—Perman & Green, LLP

(57) ABSTRACT

The present invention relates to a light scanning device for exciting and detecting secondary light, especially fluorescent light, on a sample, comprising a light-emitting device for emitting excitation light having a wavelength which is suitable for exciting secondary light on or in the sample, a scanning unit for scanning at least one subarea of the sample with said excitation light, and a detection unit for the secondary light emitted in response to excitation of the sample, said detection unit comprising a detection optics and a detector device. In the case of conventional scanning devices, the spatial resolution on the sample is determined by the scanning element alone. If spot detectors without spatial resolution are used, the detector must be read out and re-initialized after the illumination of each scanning spot on the sample; this results in a waiting time before the scanning beam can be moved to the next scanning spot and, consequently, in a reduction of the read-out velocity. For avoiding this drawback and for increasing the read-out velocity as well as for improving the spatial resolution on the sample, the device according to the present invention makes use of a detector device comprising a large number of detection elements arranged in an array with predetermined position coordinates, said detection elements being arranged in an imaging plane of the detection optics and converting light detected in spatially resolved manner into electric signals.

12 Claims, 1 Drawing Sheet

LIGHT-SCANNING DEVICE

This application is a 371 of PCT/EP97/06792, filed Dec. 4, 1997.

FIELD OF THE INVENTION

The present invention relates to a light scanning device for exciting and detecting secondary light, especially fluorescent light, on a sample, comprising a light-emitting device for emitting excitation light having a wavelength which is suitable for exciting secondary light on or in the sample, a scanning unit for scanning at least one subarea of the sample with said excitation light, and a detection unit for the secondary light emitted in response to excitation of the sample, said detection unit comprising a detection optics and a detector device.

BACKGROUND ART

Light scanning devices of the above-mentioned type are used e.g. for a spatially resolved fluorescence examination of a sample. For this purpose, the scanning light is produced in the form of a single beam by means of the light-emitting device, which is a laser in most cases, said scanning light being then directed onto the sample. By means of the scanning unit, e.g. in the form of tilting mirrors with two orthogonal tilting axes or axes of rotation in the optical path of the light beam, the beam can be rastered over the sample. The scanning light excites on the surface of the sample or in the sample the generation of secondary light, e.g. in the form of fluorescent light. This secondary light is collected via an imaging optics and detected on a detection unit. Since the scanning unit irradiates, in a precisely definable manner, a respective specific spot on the sample in dependence upon the position of the tilting mirrors relative to one another and relative to the sample, a locally dependent statement with regard to the respective property of the sample can be made by means of the detection unit detecting the intensity of the secondary light.

Since the spatial resolution is already obtained by the scanning unit, the detector device according to the prior art is a simple spot detector without spatial resolution which only detects the presence or the absence of secondary light emission independently of the point of its generation on the sample. However, after the irradiation of a specific scanning point on the sample, the irradiation of the next scanning point on the sample must be delayed until the electric signal produced by the secondary light in the photodetector has been recognized and read out and until the photodetector has been re-initialized for the next measurement. Even if a fast read-out electronics is used, this waiting time represents an undesirable delay in a fluorescence examination of a comparatively large sample to be scanned.

The scanning time for measuring the whole sample depends on various additional parameters, such as the size of the angular field on the sample, the scanning increment, the spot size of the scanning beam on the sample, the integration time of the detection unit, the scanning or mirror velocity of the scanning unit as well as the desired signal-to-noise ratio. When samples with dimensions in the centimeter range are scanned with a high spatial resolution by a scanning beam focussed to a few micrometers, the scanning times of conventional scanning devices are in the range of minutes to hours. Such long scanning times are, however, a great problem for the operation of scanning devices of this kind.

SUMMARY OF THE INVENTION

It is therefore the object of the present invention to provide an improved light scanning device which can be used for scanning a sample and for detecting secondary radiation excited by the scanning light and by means of which a faster and more efficient scanning of a large sample with high spatial resolution can be accomplished.

According to the present invention, this object is achieved by a light scanning device of the type cited at the start, which is characterized in that the detector device comprises a large number of detection elements arranged in an array with predetermined position coordinates, said detection elements being arranged in an imaging plane of the detection optics and converting light detected in a spatially resolved manner into electric signals.

In the case of the solution according to the present invention, a subarea of the sample, which depends on the magnification of the detection optics and which is scanned by the scanning light, (or the whole sample area) is imaged by means of the detection optics onto the planar detector device provided with a fieldlike array of detection elements. On the basis of the capability of detecting the secondary light in a spatially resolved manner, unequivocal imaging is guaranteed and it is guaranteed that the respective detector elements can unequivocally be associated with the corresponding area on the sample onto which the scanning light is focussed. Hence, it is possible to scan the sample subarea, which has been imaged on the detector device, without any waiting times between the individual rastering positions and to read out the whole detector device with all detection elements in common after the end of the scanning operation. This has the effect that much faster scanning is achieved than in cases in which a spot detector is used. A further advantage of the solution according to the present invention is to be seen in the fact that the accuracy of the spatial resolution on the sample is guaranteed by the resolution of the detector and is no longer influenced by tolerances which may perhaps occur in the tilting mirrors during scanning. Due to the sequential scanning of the sample with the excitation light, in the case of which the location illuminated with comparatively intensive radiation is always only one location on the sample having the size of the scanning beam, a much higher local fluorescent signal is achieved than in cases where a full-area illumination of the sample is carried out. It follows that the provision of a dual spatial resolution by the scanning unit as well as by the detector device leads, on the one hand, to an increase of the fluorescent signal of the respective scanning spot and, on the other hand, still to a drastic reduction of the scanning time required for a sample having a comparatively large surface, said dual spatial resolution being not known in the prior art.

A further advantage of the device according to the present invention is to be seen in the fact that imaging errors of the detection optics can be determined e.g. with the aid of a testing method, which is carried out once and which is executed e.g. with the aid of a test grating, such as a Ronchi grating, and that these imaging errors can subsequently be used for image correction. This permits the use of simple lenses for the detection optics, which are corrected to a comparatively low degree and which are therefore less expensive.

According to a preferred further development of the present invention, the detection optics is a varifocal optics with variable magnification in the case of which a variable sample area is imaged onto the constant detector area. It is thus possible to adjust the resolution in a comparatively simple manner while varying the scanning area accordingly. If a reducing image scale is used, a survey of a larger area can be obtained without any necessity of changing the scanning carried out by the scanning unit. If, however, a enlarged image is used, details can be made visible on the sample area again without any change of the scanning conditions produced by the scanning unit.

In the above-mentioned further development, it will be particularly advantageous to provide a sample holder which is adapted to be displaced in at least one direction relative to the optical axis of the scanning light. When details of the sample are examined, different areas of the sample can be moved into the object plane of the detection optics by means of this arrangement.

According to an additional advantageous further development of the present invention, the detection optics comprises a first lens and a second lens which are arranged in spaced relationship with each other. Additional optical elements for processing or influencing the secondary light can be provided between the two spaced-apart lenses. A cut-off filter for suppressing the excitation light is advantageously provided between the lenses. In this connection, it is especially of advantage that the first lens, by means of which the secondary light emitted by the sample and also excitation light scattered in the sample is detected, shows telecentricity on the image side, i.e. that the exit pupil is infinitely far away. The whole object area is imaged at infinity. Due to the telecentricity of the image-side beam, all light rays impinge at a constant angle of incidence upon the cut-off filter arranged between the two lenses so that the perpendicular incidence required for interference filters is guaranteed.

According to an additional advantageous embodiment, a focussing optics is provided for focussing the excitation light onto the sample. This permits a further increase in the spot intensity of the excitation light, whereby the resolution and the intensity of the secondary light will be increased. The focussing optics should advantageously be an F/Θ lens in the case of which the scanning beam is imaged according to the so-called F/Θ condition $y'=F \times \Theta$, wherein $y'$ is the imaging coordinate, $F$ the focal length and $\Theta$ the angle enclosed by the scanning beam and the optical axis. This guarantees a porportionality between the scanning angle and the image height $y'$ and simultaneously also a proportionality between the angular velocity of the deflection system and the scanning velocity of a sample plane. It follows that, when the angular velocity of the scanning mirrors is constant, a constant excitation intensity on the sample will be created, independently of the scanning position, due to the linearity between the scanning velocity on the sample and the angular velocity.

According to another advantageous further development, the scanning unit comprises two tilting mirrors whose axes of rotation extend perpendicular to one another, said tilting mirrors being used for scanning the sample with the excitation light.

According to an additional advantageous further development of the present invention, a read-out and processing circuit is provided for reading the array of detection elements and for accumulating successive output values of corresponding detection elements for successive read-out operations. When the sample is scanned several times or continuously with the scanning light, the scanning operation can be observed online when the read-out values are being accumulated, whereby it is, for example, possible to watch changes on the sample occurring e.g. due to kinetic processes.

In a further advantageous embodiment, a division device is provided for dividing the excitation light into a plurality of scanning beams for simultaneously scanning the sample. Due to the use of the detector with spatial resolution, secondary light emission can be excited at several points on the sample simultaneously, an unequivocal local association of the secondary light generated being still possible. Hence, the scanning velocity can be increased still further.

Further advantgeous embodiments are disclosed in the sub-claims.

BRIEF DESCRIPTION OF THE DRAWINGS

Making reference to the accompanying drawing, the present invention will be explained and described in more detail on the basis of an advantageous embodiment. In the said drawing.

DETAILED DESCRIPTION OF THE PREFERRED EMBODIMENT

Figure 1:
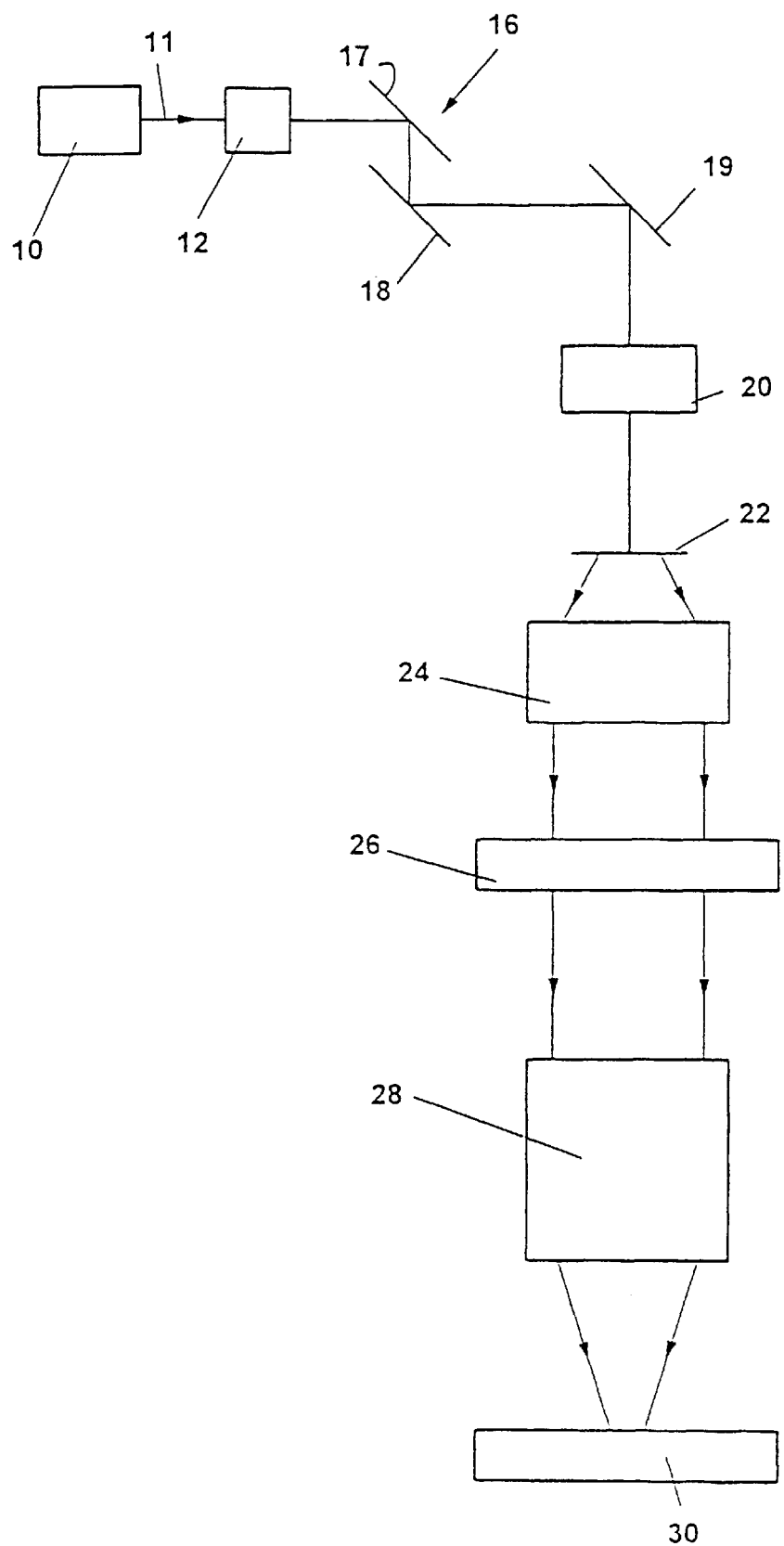
FIG. 1 shows a schematic representation of the scanning device according to the present invention.

In the embodiment shown in the drawing, a light-generating device 10, e.g. a laser, is provided, which emits scanning light with a specific wavelength in the form of a beam 11. For forming and modifying the beam 11, a beam forming device 12 is provided by means of which the beam can be expanded and/or spatially filtered. Further along the ray path of the beam 11, the beam forming device 12 is followed by a scanning unit 16 comprising two tilting mirrors 17 and 18 which have orthogonal axes of rotation and tilting axes, respectively. The beam is reflected at the tilting mirrors 17 and 18 and guided to a further deflection mirror 19, where the scanning light is reflected to a focussing optics 20 and then focussed onto a sample 22.

If the light-emitting device 10 is arranged such that the beam 11 is initially parallel to the incidence direction of the focussed scanning light, it will be possible to dispense with the deflection mirror 19.

In the arrangement shown in FIG. 1, the secondary light emitted by the sample 22 is detected in the semispace facing away from the excitation side, i.e. in a translucent measuring procedure. For this purpose, a detection optics comprising a first lens 24 and a second lens 28 is provided by means of which an area on the sample 22 is imaged onto a detector 30.

The detector 30 is preferably an efficient CCD detector comprising a large number of very small detection elements which have dimensions in the micrometer range and which are arranged in a fieldlike array with fixed determination of their position coordinates.

The first lens 24 of the detection optics is preferably a widely open lens with a short focal length, which images the object area on the sample at infinity. The first lens shows telecentricity on the image side. Preferably, the first lens has a high definition over the whole object field, a property which can be achieved by suitable image correction measures.

In the space between the first lens 24 and the second lens 28, a cut-off filter 26 is preferably arranged, said cut-off filter 26 being used for suppressing excitation light transmitted through the sample and having a wavelength which is different from, viz. shorter than that of fluorescence. Due to the telecentricity of the beam between the two lenses 24 and 28, the function of the cut-off filter 26 is optimized, since the light has a constant angle of incidence.

By means of the second lens 28 an image of the object area on the sample is formed on the detector device 30 making use of the telecentric beam produced by the first lens 24. The combination of the first lens 24 and of the second lens 28 is, advantageously, implemented in such a way that the sample area of interest will fully illuminate the predetermined area of the detector device. In this connection, it will especially be of advantage when the system has a variable image scale so that the sample area of interest and, consequently, the magnification of the sample can be varied.

It will be advantageous when the focussing optics 20 used for focussing the scanning light onto the sample is an F/Θ lens which, independently of the displacement, i.e. the distance from the optical axis, focusses the beam sharply to spot sizes in the micrometer range on the sample 22. When an F/Θ lens is used, the scanning beam is imaged according to the so-called F/Θ condition y'=FxΘ, wherein y' is the imaging coordinate, F the focal length and Θ the angle enclosed by the scanning beam and the optical axis. In contrast to conventional lenses, where the normally applicable condition y'=Fxtan Θ holds true, the F/Θ lens causes a barrel distortion. This guarantees a proportionality between the scanning angle and the image height y' and simultaneously also a proportionality between the angular velocity of the deflection system and the scanning velocity in the sample plane. It follows that, when the angular velocity for the deflection of the beam is constant, a constant excitation intensity on the sample will be created, independently of the scanning position, due to the linearity between the scanning velocity on the sample and the angular velocity.

This kind of arrangement of the focussing optics between the scanning unit 16 and the sample 22 is referred to as "pre-objective scanning". This is used more frequently than "post-objective scanning" where the focussing optics is arranged in the optical path in front of the deflection unit 10 so that the scanning light, which is convergent after the focussing optics, is deflected via the scanning mirrors and directed onto the sample 22. In the case of this kind of arrangement of the focussing optics in front of the scanning unit 16, the lens only has to fulfil minimal demands. It may have a small diameter and it only has to form sharp images in the paraxial region. The deflection unit arranged behind the lens results, however, in a curved scanning line located on a circular arc about the axis of rotation of the tilting mirror. This "post-objective scanning" arrangement is therefore not preferred for scanning plane surfaces.

Hence, it will be advantgeous to use the "pre-objective scanning" arrangement comprising an F/e lens, which can be used for forming images in a plane with an image coordinate that is proportional to the deflection angle. The F/Θ lens in the "pre-objective scanning" arrangement must, however, have a comparatively large diameter so that it will also accept scanning beams having a large scanning angle. It must also be corrected over a comparatively large angular field according to the tilting of the light beam relative to the axis and, in addition, it must have a good field flatness.

The sample is preferably arranged on a carriage which is adapted to be displaced in at least one direction at right angles to the optical axis of the excitation light. The sample can in this way be loaded onto and unloaded from the carriage and, in addition, the respective sample area of interest can be positioned in the object field of the detection optics in the case of a high magnifying power of the detection optics with which it is no longer possible to image the whole area of the sample onto the detector device.

Whereas the arrangement shown in FIG. 1 uses the translucent measuring procedure, it would also be possible to detect the secondary light in a reflective arrangement. For this purpose, a beam splitter, preferably a dichroic beam splitter, would have to be provided in the optical path of the excitation light. The dichroic beam splitter is essentially transparent either for the laser light or for the secondary light, which have predetermined different wavelengths, whereas the respective other light is reflected. In this embodiment the deflection mirror 19 may a dichroic mirror, for example.

When the scanning device according to the present invention is in operation, the whole sample area will be rastered; due to the 1:1 association between the sample area and the image area on the detector device, a fluorescent signal will only be produced at a position corresponding to a sample location emitting secondary light. When the scanning has been finished, a locally distributed detection of secondary light from the sample exists in the detector, which can be read out and used for further processing.

Possible imaging errors of the detection optics can be determined with the aid of a testing method, using e.g. a test grating such as a Ronchi grating, stored and subsequently be used for image correction during further processing. Possibly existing different sensitivities of the individual detection elements, both spectrally and as regards the intensity, can also be measured once without a sample and with constant light illumination and can be stored in a correction table and used for further processing the read-out measurement results.

The reading of the detector device can be executed asynchronously with the scanning, the signals of identical detection elements being accumulated for successive scannings. When several or all detection elements (frame) are read, the scanning (or the repeated scanning) can be observed on-line on the basis of the accumulating representation, whereby possibly occurring kinetic processes can be watched. After the reading, the detection elements are re-initialized (reset) so that non-illuminated detection elements will be prevented from integrating a dark signal. The suppression of the dark value is independent of the integration time, i.e. the time between two successive readings. For combining the accumulating representation with the new initialization after each reading, an operation of the logic OR-function type is advantageously provided for each pixel between successive readings.

Since an unequivocal association sample position/detector location exists and since the laser position is also known at any time, reading could be carried out as follows: after each rastered line, the scanner transmits a triggering pulse to the read-out electronics of the CCD so that only the current, illuminated line is read and the chip is reset subsequently. This has the advantage that the dark current integration lasts only for the duration of one line but not for the scanning of the whole sample. Each triggering pulse increments the electronics so that the next line can be read. When the n-th line is acted upon, n lines must be displaced towards the next possible edge of the chip (to the read-out register). The device according to the present invention is so conceived that each side of the chip, which is divided in two halves, has associated therewith a readout register. When a line located e.g. above the middle is read, the charges will be shifted into the read-out register of the upper half and when a line located below the middle is read, the charges will be shifted into the read-out register of the lower half.

For achieving the best focussing of the scanning light on the sample and for focussing the scanning light on samples of different thicknesses, the focussing can be readjusted by adjusting the beam expansion in the expansion device 12 while supervising the image patch obtained on the detector device. Optimum focussing exists when a minimum image patch is produced on the detector device.

In comparison with the prior art, the device according to the present invention achieves the advantage that a sample can be scanned more rapidly, since the reading of the detector for each scanning spot on the sample, which has been necessary in the case of the spot detectors that have normally been used up to now, and a resultant waiting time prior to conducting the beam to the next scanning spot are no longer necessary. In the device according to the present invention, the spatial resolution is only limited by the density and the size of the detection elements, the quality of the lenses and the image scale, but it is neither limited by the scanning intervals nor by the scanning rate.

What is claimed is:

1. A light scanning device for exciting and detecting secondary light of a sample, comprising:
    a light-emitting device for emitting excitation light having a wavelength which is suitable for exciting secondary light on or in the sample,
    a scanning unit for scanning at least one subarea of the sample with said excitation light, and
    a detection unit for the secondary light emitted in response to excitation of the sample, said detection unit comprising a detection optics and a detector device,
    wherein the detector device comprises a large number of detection elements arranged in an array with predetermined position coordinates, said detection elements being arranged in an imaging plane of the detection optics and converting light detected in a spatially resolved manner into electric signals, and
    the detection optics is a varifocal optics with variable magnification arranged so that the image field size on the detector can be kept constant and the object field size on the sample can be varied.

2. The light scanning device according to claim 1, wherein the detector device is a CCD chip.

3. The light scanning device according to claim 1, wherein the detection optics comprises a first lens and a second lens which are arranged in spaced relationship with each other.

4. The light scanning device according to claim 3, wherein the first lens, by means of which the secondary light emitted by the sample is image, is telecentric on the image side.

5. The light scanning device according to claim 4, wherein a cut-off filter for suppressing the excitation light is provided between the first and the second lens.

6. The light scanning device according to claim 1, wherein the light-emitting device is a laser.

7. The light scanning device according to claim 1, further comprising a division device for dividing the excitation light into a plurality of scanning beams for simultaneously scanning the sample.

8. A light scanning device for exciting and detecting secondary light of a sample, comprising:
    a light-emitting device for emitting excitation light having a wavelength which is suitable for exciting secondary light on or in the sample,
    a scanning unit for scanning at least one subarea of the sample with said excitation light,
    a detection unit for the secondary light emitted in response to excitation of the sample, said detection unit comprising a detection optics and a detector device,
    wherein the detector device comprises a large number of detection elements arranged in an array with predetermined position coordinates, said detection elements being arranged in an imaging plane of the detection optics and converting light detected in a spatially resolved manner into electric signals, and
    a sample holder which is adapted to be displaced in at least one direction relative to the optical axis of the scanning light.

9. A light scanning device for exciting and detecting secondary light of a sample, comprising:
    a light-emitting device for emitting excitation light having a wavelength which is suitable for exciting secondary light on or in the sample, the excitation light being produced in the form of a light beam,
    a beam expansion unit for expanding beam cross-section,
    a scanning unit for scanning at least one subarea of the sample with said excitation light, and
    a detection unit for the secondary light emitted in response to excitation of the sample, said detection unit comprising a detection optics and a detector device,
    wherein the detector device comprises a large number of detection elements arranged in an array with predetermined position coordinates, said detection elements being arranged in an imaging plane of the detection optics and converting light detected in a spatially resolved manner into electric signals.

10. A light scanning device for exciting and detecting secondary light of a sample, comprising:
    a light-emitting device for emitting excitation light having a wavelength which is suitable for exciting secondary light on or in the sample,
    a scanning unit for scanning at least one subarea of the sample with said excitation light the scanning unit comprising two tilting mirrors with axes of rotation extending perpendicular to one another, said tilting mirrors being used for scanning the sample with the excitation light,
    a detection unit for the secondary light emitted in response to excitation of the sample, said detection unit comprising a detection optics and a detector device,
    wherein the detector device comprises a large number of detection elements arranged in an array with predetermined position coordinates, said detection elements being arranged in an imaging plane of the detection optics and converting light detected in a spatially resolved manner into electric signals.

11. A light scanning device for exciting and detecting secondary light of a sample, comprising:
    a light-emitting device for emitting excitation light having a wavelength which is suitable for exciting secondary light on or in the sample,
    a focussing optics for focussing the excitation light onto the sample, the focussing optics comprising and F/θ lens,
    a scanning unit for scanning at least one subarea of the sample with said excitation light, and
    a detection unit for the secondary light emitted in response to excitation of the sample, said detection unit comprising a detection optics and a detector device,
    wherein the detector device comprises a large number of detection elements arranged in an array with predetermined position coordinates, said detection elements being arranged in an imaging plane of the detection optics and converting light detected in a spatially resolved manner into electric signals.

12. A light scanning device for exciting and detecting secondary light of a sample, comprising:

a light-emitting device for emitting excitation light having a wavelength which is suitable for exciting secondary light on or in the sample, a scanning unit for scanning at least one subarea of the sample with said excitation light, a detection unit for the secondary light emitted in response to excitation of the sample, said detection unit comprising a detection optics and a detector device, wherein the detector device comprises a large number of detection elements arranged in an array with predetermined position coordinates, said detection elements being arranged in an imaging plane of the detection optics and converting light detected in a spatially resolved manner into electric signals, and a read-out and processing circuit for reading the array of detection elements and for accumulating successive output values of corresponding detection elements for successive read-out operations, the read-out and processing circuit additionally comprising, for each detection element, a circuit of the logic or circuit type for suppressing successive dark values.

* * * * *